United States Patent
Moskal

(10) Patent No.: US 10,432,403 B2
(45) Date of Patent: Oct. 1, 2019

(54) SECURE COMMUNICATION BETWEEN INFUSION PUMP AND SERVER

(71) Applicant: Fenwal, Inc., Lake Zurich, IL (US)

(72) Inventor: Witold Moskal, Park Ridge, IL (US)

(73) Assignee: Fenwal, Inc., Lake Zurich, IL (US)

( * ) Notice: Subject to any disclaimer, the term of this patent is extended or adjusted under 35 U.S.C. 154(b) by 333 days.

(21) Appl. No.: 15/331,373

(22) Filed: Oct. 21, 2016

(65) Prior Publication Data

US 2017/0149567 A1 May 25, 2017

Related U.S. Application Data

(60) Provisional application No. 62/259,826, filed on Nov. 25, 2015.

(51) Int. Cl.
| | |
|---|---|
| *H04L 29/06* | (2006.01) |
| *H04L 9/32* | (2006.01) |
| *A61M 5/142* | (2006.01) |
| *G06F 21/64* | (2013.01) |
| *H04W 12/10* | (2009.01) |
| *G16H 40/67* | (2018.01) |
| *G16H 20/17* | (2018.01) |

(52) U.S. Cl.
CPC .......... *H04L 9/3236* (2013.01); *A61M 5/142* (2013.01); *G06F 21/64* (2013.01); *G16H 20/17* (2018.01); *G16H 40/67* (2018.01); *H04L 9/3239* (2013.01); *H04L 9/3242* (2013.01); *H04L 63/123* (2013.01); *H04W 12/10* (2013.01); *A61M 2205/3584* (2013.01); *A61M 2205/50* (2013.01)

(58) Field of Classification Search
CPC ... H04L 9/3236; H04L 9/3239; H04L 9/3242; H04L 63/123; G16H 40/63; G06F 21/64; G06F 19/00; H04W 12/10
See application file for complete search history.

(56) References Cited

U.S. PATENT DOCUMENTS

| | | | | |
|---|---|---|---|---|
| 5,807,336 A | * | 9/1998 | Russo | A61M 5/172 604/131 |
| 6,519,569 B1 | * | 2/2003 | White | A61M 5/142 705/3 |

(Continued)

OTHER PUBLICATIONS

European Search Report and Annex for European App. No. 16197656.8 dated Jan. 25, 2017, 8 pages.

(Continued)

*Primary Examiner* — John B King
(74) *Attorney, Agent, or Firm* — Becker Patent Law, LLC

(57) ABSTRACT

An infusion pump and server computer have improved network access security. The infusion pump has a network interface circuit to provide communications over a network and a processing circuit that generates infusion pump data for transmission to a remote server computer. The processing circuit generates a header portion of a request message having at least one field, hashes the header portion but not payload data using a cryptographic hash function and a cryptographic key to provide a hashed code, and inserts the hashed code into the header portion of the request message. The processing circuit inserts the infusion pump data into a body portion of the request message and transmits the request message to the remote server computer over the communications network.

18 Claims, 6 Drawing Sheets

(56) References Cited

U.S. PATENT DOCUMENTS

| | | | | |
|---|---|---|---|---|
| 6,525,850 | B1* | 2/2003 | Chang | H04J 14/0227 370/352 |
| 6,816,596 | B1* | 11/2004 | Peinado | G06F 21/10 380/277 |
| 7,300,418 | B2* | 11/2007 | Zaleski | A61M 5/172 604/131 |
| 7,814,546 | B1* | 10/2010 | Strayer | H04L 63/1416 726/23 |
| 8,146,149 | B2* | 3/2012 | Steinkogler | G06F 19/3418 726/16 |
| 8,348,885 | B2* | 1/2013 | Moberg | A61B 5/0002 604/65 |
| 8,412,841 | B1* | 4/2013 | Swaminathan | H04L 65/4084 709/231 |
| 9,215,075 | B1* | 12/2015 | Poltorak | H04L 63/04 |
| 2004/0255114 | A1 | 12/2004 | Lee | |
| 2005/0135306 | A1* | 6/2005 | McAllen | H04L 29/06 370/329 |
| 2005/0138428 | A1* | 6/2005 | McAllen | H04L 29/06 726/4 |
| 2006/0069787 | A1* | 3/2006 | Sinclair | G06F 17/3089 709/229 |
| 2006/0264202 | A1* | 11/2006 | Hagmeier | H04L 63/0823 455/411 |
| 2008/0005558 | A1 | 1/2008 | Hadley et al. | |
| 2008/0075079 | A1 | 3/2008 | Smith | |
| 2009/0103715 | A1* | 4/2009 | Thorbjornsson | G06F 17/3033 380/28 |
| 2009/0150438 | A1* | 6/2009 | Markisohn | G16H 10/60 |
| 2010/0082984 | A1 | 4/2010 | Ellison | |
| 2012/0331308 | A1* | 12/2012 | Fernandez Gutierrez | G06F 21/71 713/190 |
| 2013/0024688 | A1* | 1/2013 | Wen | H04L 63/0807 713/168 |
| 2013/0064104 | A1* | 3/2013 | Bekiares | H04L 63/1466 370/252 |
| 2014/0108800 | A1* | 4/2014 | Lawrence | H04L 9/3297 713/168 |
| 2014/0195639 | A1* | 7/2014 | Kamen | G06F 19/3418 709/217 |
| 2014/0341029 | A1 | 11/2014 | Allan et al. | |
| 2016/0099922 | A1* | 4/2016 | Dover | H04L 63/061 713/171 |
| 2017/0141926 | A1* | 5/2017 | Xu | H04L 9/3263 |
| 2018/0048731 | A1* | 2/2018 | Yeager | H04L 67/2842 |
| 2018/0316511 | A1* | 11/2018 | Meyer | H04L 9/3268 |

OTHER PUBLICATIONS

RFC 7235—Hypertext Transfer Protocol (HTTP/1.1): Authentication, printed from the Internet at http://tools.ietf.org/html/rfc7235#section4.2 on Nov. 20, 2015, 38 pages.

* cited by examiner

SECURE COMMUNICATION BETWEEN INFUSION PUMP AND SERVER

BACKGROUND

Infusion pumps are used to administer drugs and other medicaments to patients, typically in a clinical setting. An infusion pump provides a controlled amount of the medicament over time to the patient. The amount is administered pursuant to parameters entered by a clinician into the pump using a pump user interface.

Some infusion pumps can be monitored or controlled remotely over a network. This introduces the potential of a security threat, since a cyber attacker could take remote control of the system and change the amount of medicament administered to a patient.

Infusion pumps typically have less processing power than computer servers. Complex or processor-intensive encryption algorithms may be impracticable for some infusion pumps.

DETAILED DESCRIPTION OF ILLUSTRATIVE EMBODIMENTS

One or more embodiments described herein may provide privacy and/or data integrity using a secret key between server and pump communication.

One or more embodiments described herein may provide a secure communication that can be implemented on a device that cannot fully implement the Transport Layer Security (TLS).

One or more embodiments described herein may use a Hash Message Authentication Code (HMAC) between a server computer and an infusion pump to provide communications security over networks in spite of computing power constraints of the infusion pump.

One or more embodiments described herein may provide for authentication between a sender and recipient and/or data integrity.

One or more embodiments described herein use a hash function over only a header portion of a message, since the header may carry sensitive information about the message body.

One or more embodiments described herein may use time of day to help deter spoofing.

Figure 1:
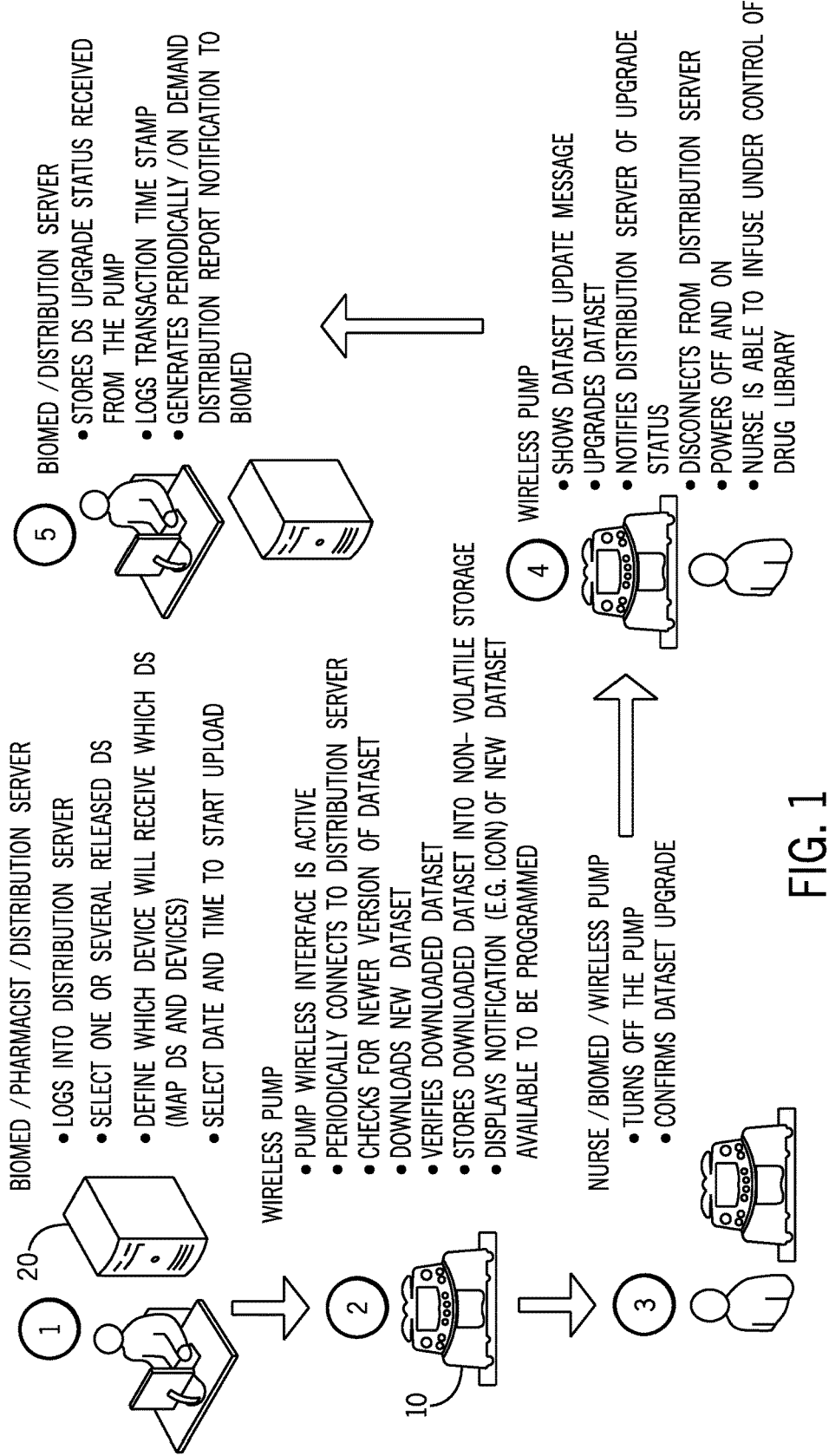
FIG. 1 is a flow diagram of a system and method for programming a dataset from a server computer to an infusion pump, according to an illustrative embodiment.

Referring now to FIG. 1, a flow diagram of a system for programming an infusion pump with a dataset from a server computer will be described. Infusion pump 10 may be any of a variety of infusion pumps, such as a large volume infusion pump, a patient-controlled analgesia (PCA) pump, elastomeric pump, syringe pump, enteral or parenteral feeding pump, insulin pump, etc. At Step 1 in FIG. 1, a user (e.g., a pharmacist, biomedical engineer, etc.) logs into a server computer 20 or terminal in communication with server computer 20. The user selects one or more datasets to be programmed into or downloaded to infusion pump(s) 10. The dataset may comprise data that the infusion pump uses in its operation. For example, the dataset may be a library of drug programming parameters that provide default values and limits to a user's ability to program the infusion pump. For example, a data set may comprise hard limits and/or soft limits to different pump programming parameters, such as infusion rate, dose, infusion time or duration, etc. The limits of the data set may be different for different drugs, and may include a "drug X" data set for a drug not known by the data library. Once changes are made to the data set or library, server 20 may be used to remotely download, update, or otherwise program infusion pumps 10 (e.g., by care area, universally, etc.) with the new data set created by the pharmacist or other user. The user may select a date and time after which the infusion pump will receive the new dataset.

At Step 2, in FIG. 1, infusion pump 10 may be configured for wired and/or wireless communication with a server computer 20. Each of pump 10 and server computer 20 may comprise a network interface circuit configured for network communications, such as a Wi-Fi circuit, Bluetooth circuit, Ethernet card, or other network interface circuit. Pump 10 is configured to transmit and server 20 is configured to receive a request for infusion pump data, such as a dataset, such as a library of infusion data. Infusion pump data requests may be initiated by infusion pump 10 and may occur periodically, intermittently, occasionally, every few minutes, several times per day, or at other regular or irregular frequencies. Pump 10 may be configured to request whether a newer version of a dataset is available for download from server computer 20 and to download the dataset. The downloaded dataset may be stored in non-volatile storage memory. Pump 10 may be configured to display a notification (e.g., an icon or other notification) that a new dataset is downloaded and available to be programmed.

At Step 3 of FIG. 1, a nurse, biomedical engineering staff, or other user may, upon seeing the notification, cycle the power on the pump to install the new dataset. Pump 10 may be configured to confirm via a notification that a dataset is available for upgrading or updating. At Step 4, a user may command the pump to upgrade the dataset. Once the dataset is upgraded, pump 10 may notify server computer 20 of upgrade status (e.g., upgrade complete or successful, upgrade failed or error, etc.). Pump 10 may then disconnect from communications with server computer 20 for security purposes. After cycling the power, the nurse is able to infuse under control of the new dataset downloaded.

At Step 5, server computer 20 is configured to store the upgrade status received from pump 10, log the transaction time stamp (e.g., the time the pump was upgraded, the time the upgrade confirm message was received, or other time), and generate on demand or periodically a distribution report notification to another user, such as a biomedical engineering staff. Reports may be generated in a prescheduled manner or on-demand based on user inputs to the system. Reports may also be sent automatically, without requiring user input, on a scheduled basis, or in response to certain rules being met (e.g., alarm triggered, a certain number of alarms triggered, a certain number of override or reprogram events, etc.).

FIG. 1 is one illustration of an environment in which secure communications described herein may be used. Alternate environments are contemplated, such as the reporting of infusion data events from pump 10 to server 20, or other wireless or wired data transmissions or exchanges, such as monitoring, control, updating, provisioning, backup, restore, or other functions.

Figure 2:
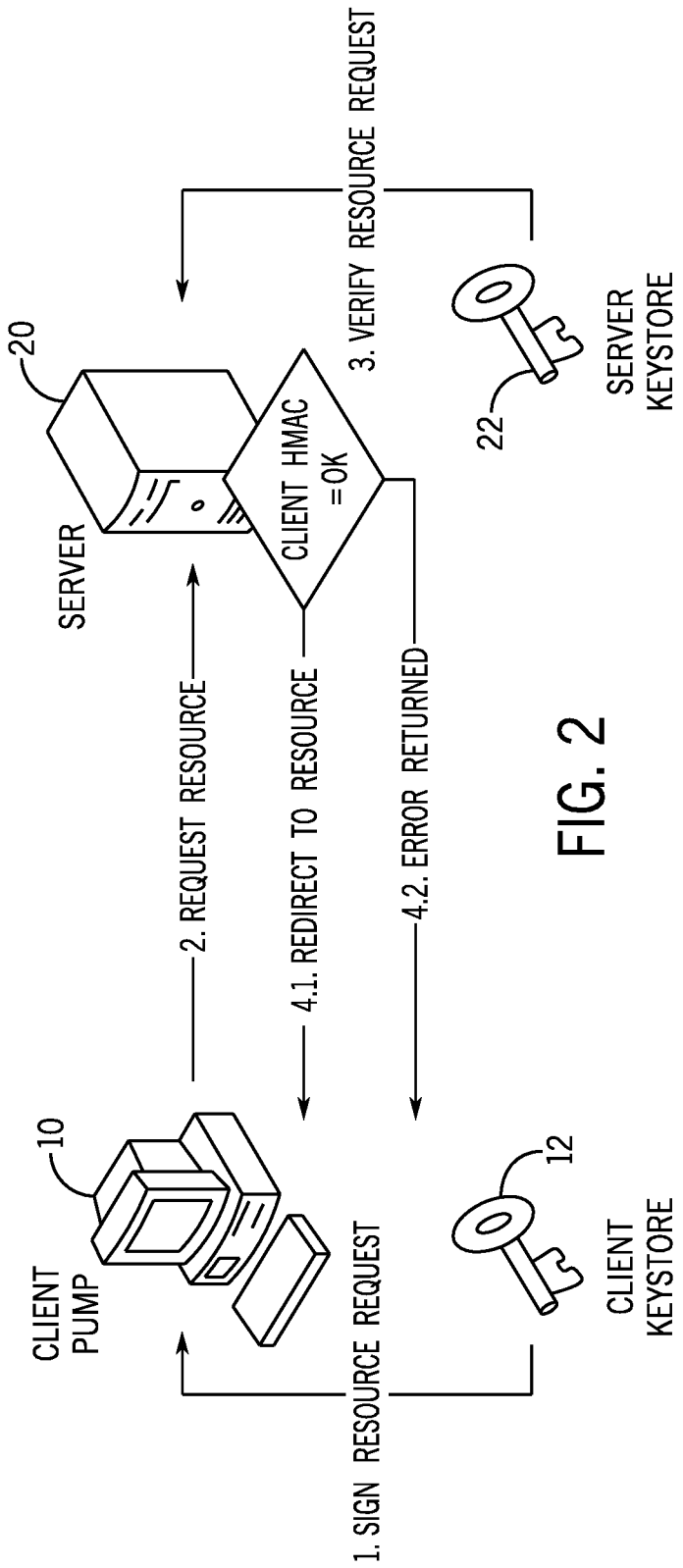
FIG. 2 is flow diagram of a system and method for providing secure communications between an infusion pump and a server computer, according to an illustrative embodiment.

Referring now to FIG. 2, systems and methods for providing secure network access to an infusion pump will be described. As mentioned, each of pump 10 and server 20 comprises a network interface circuit configured for communication over a network, such as a hospital network. Routers or other networking components may be provided in the communication chain between pump 10 and server 20. In one embodiment, the interface between server 20 and pump 10 follows a strict client-server model of communication, in which pump 10 is always in the role of a client and the server is always in the role of a server computer. In alternative embodiments, the devices may change client and server roles, for example at different times or in different modes.

In an exemplary client-server model, the server component provides a function or service to one or many clients which initiate requests for services. Clients and servers may exchange messages in a request-response messaging pattern: client sends a request and the server returns a response. A HTTP protocol may be used in the application layer for the communication between the server and client pumps. Once a transmission control protocol (TCP) connection is created, two steps in communication comprise Request and Response. Pursuant to HTTP RFC, during a Request, the HTTP client sends a request message that specifies the resource that the client wishes to retrieve from the server and/or reports information to the server. During the Response, the HTTP server reads and interprets the request from the client. The server takes action relevant to the request and sends an HTTP Response message back to the client. The response message contains the content of the resource that the client requested, if appropriate.

In this exemplary embodiment, client pump 10 may be configured to generate a request message and electronically sign it at step 1 of FIG. 2. The request message may be signed electronically using a cryptographic key which has been shared out of bounds or out-of-band with server 20. Out-of-band communication may refer to a second communication channel that is separate and unconnected from a communication channel used to transmit the request from client pump 10. Each pump 10 and server 20 relationship may comprise a separate shared cryptographic key, the keys being stored in a client keystore 12 on the client side and a server keystore 22 on the server side. For example, one server 20 may store a different cryptographic key for each pump 10 it communicates with, and vice versa.

In this embodiment, the electronic signing at step 1 is done using a Hash Message Authentication Code (HMAC) method based on an SHA-1 cryptographic hashing algorithm built into the communication protocol. In this HMAC-based authentication, client pump 10 creates a HMAC for the resource request message. At step 2, client pump 10 requests access to a resource with a signed request. At step 3, server 20 verifies client's request by comparing received and computed HMAC values. The computed HMAC value may be generated using the shared key retrieved from server keystore 22 (step 3). The computer HMAC value may be generated by hashing the same portion of the request message that was hashed by client pump 10. If the computed HMAC value matches the received HMAC value, server 20 grants access to the resource requested by the client (step 4.1). If not, the server may return an error (step 4.2).

According to one advantageous aspect, pump 10 initiates all communication requests with server 10 so that the risk of a cyberattack, such as a brute force attack, is minimized. Server may be configured to not make requests or commands on its own initiative, in keeping with a strict client/server model of communication. In one embodiment, pump 10 may be configured to block commands from any server computer which are not sent in response to the request for command transmitted by the infusion pump.

One mechanism for preventing cyberattacks on pump 10 is to close one, more or all of the communication ports provided by the network interface circuit of pump 10. A port may be an end-point of a communication, in software form, hardware form, or both. For example, in transmission control protocol/internet protocol (TCP/IP), a port is opened before communication may occur. By closing a communication port, a device does not receive communications on that port and therefore cannot be attacked. Another mechanism that may be used is a firewall, in which a software construct monitors communications and determines whether the communications should be received by the device. Yet another mechanism that may be used is a proxy, which is a program that evaluates incoming traffic to determine if it is safe for a network. Any of these mechanisms or other mechanisms may be used to block attempts to communicate with client pump 10.

Figure 3:
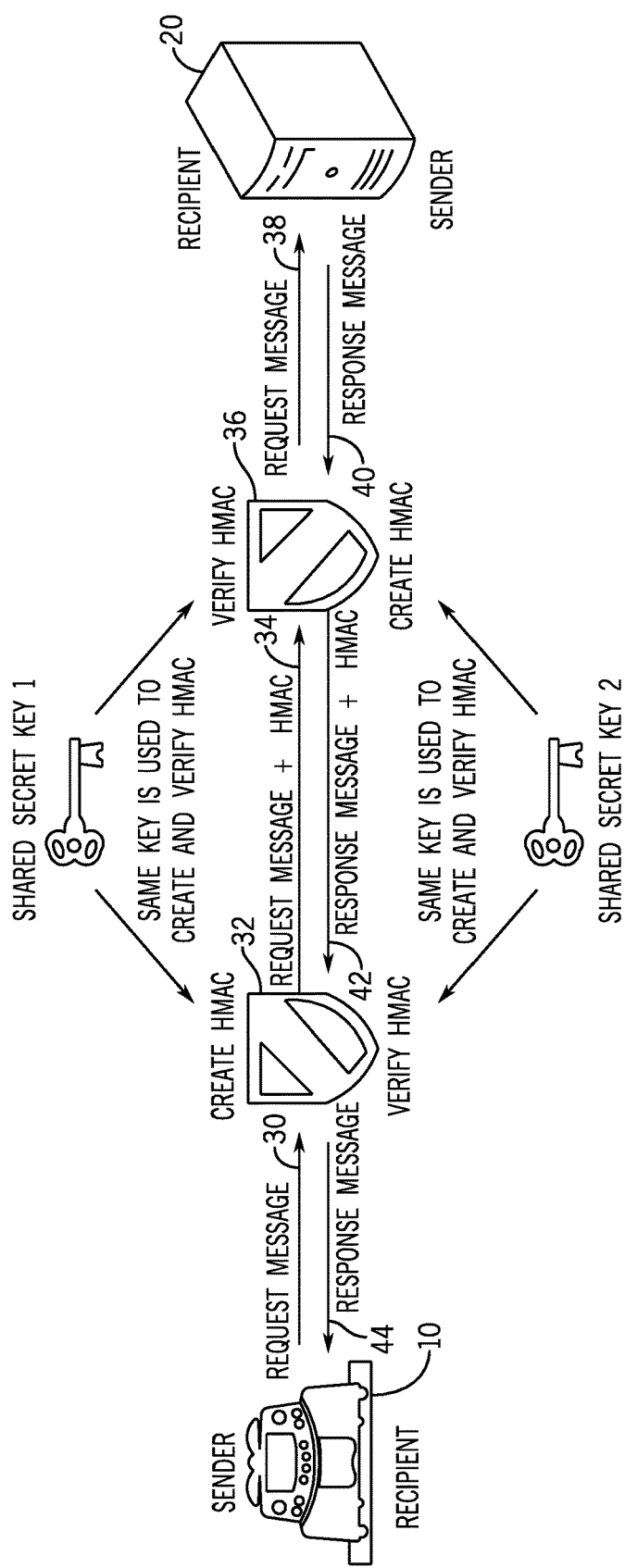
FIG. 3 is a flow diagram of a system and method for providing secure communications between an infusion pump and a server computer, according to an illustrative embodiment.

Referring now to FIG. 3, a flow diagram of a system and method for providing secure communications between an infusion pump and a server computer will be described. Client pump and server computer may both use an HMAC method for authentication in Hypertext Transfer Protocol (HTTP) messages (i.e. Requests and Responses) they send and receive. The message integrity and authentication may implement a custom authentication scheme around the HTTP extension-header "Authorization" header using a custom HMAC. The message sender (client/server) may use the supplied secret key to sign and encrypt all requests according to SHA-1 (Secure Hash Algorithm 1) algorithm. The recipient (server/client) may use the same secret key and algorithm to authenticate the sender.

At line 30, pump 10 may be configured to generate a request message. The request message may be generated according to an HTTP format, for example, comprising a request line, one or more headers, a body for containing a payload, and/or other fields. HTTP headers include a general-header, request-header, response-header, and entity-header fields. Each header field may comprise a name followed by a colon (":") and the field value. Headers may define the operating parameters of an HTTP transaction. The header fields may be transmitted after a request or response line, which may be the first line of a message. Header fields may be colon-separated name-value pairs in clear-text string format, terminated by a carriage return (CR) and line feed (LF) character sequence. The end of the header section may be indicated by an empty field, resulting in the transmission of two consecutive CR-LF pairs.

Pump 10 may be configured to generate an HMAC of a portion of the request message at block 32 using a first secret cryptographic key shared with server 20 (preferably shared out of bounds prior to the communication). At line 34, the request message and HMAC code or value are transmitted to server 20.

At block 36, server 20 may be configured to use a portion of the request message and the first shared secret key to generate an HMAC code or value and compare the generated HMAC code to the received HMAC code. If the codes match, as shown at line 48, the request message is processed by server 20.

When generating a response message (line 40), which may also be in HTTP format, server 20 may be configured to use the same or a similar algorithm as was used at block 32 in its block 36. In this case, a second, different, shared cryptographic key may be used to create an HMAC of a portion of the response message. At line 42, the response message and generated HMAC value 42 may be transmitted to block 32 which uses the client-side second shared secret key to HMAC the same portion of the response message for comparison to the HMAC received from server 20. If the HMAC codes match, at line 44, the response message is processed by pump 10.

Figure 4:
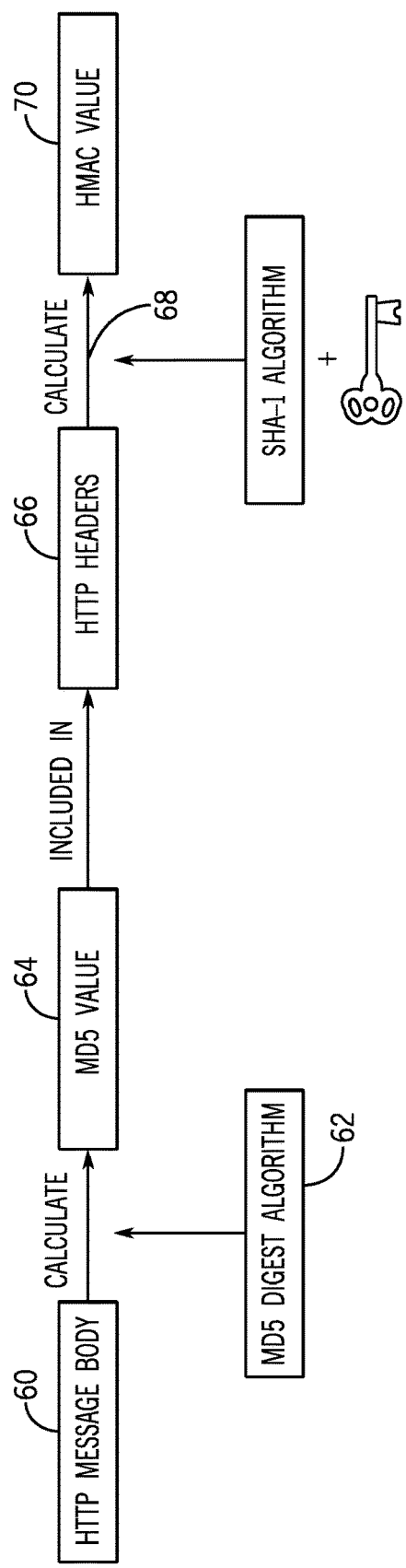
FIG. 4 is a flowchart of a method of generating a secure communication, according to an illustrative embodiment.

Referring now to FIG. 4, an exemplary method of constructing a request message will be described. At block 60, a body or payload portion of an HTTP message body is generated or provided by a processing circuit. A Message Digest 5 (MD5) algorithm 62 may be used to generate an MD5 value 64 based on the HTTP message body portion. In one example, the MD5 algorithm may generate a 128-bit (16-byte) hash value, which may be expressed in text format as a 32 digit hexadecimal number.

At block 66, the MD5 value is included in or inserted into one or more header portions of an HTTP request message. A second hash function is provided at line 68 using, in this case, an SHA-1 algorithm and a secret cryptographic key shared with the recipient of the communication. The second hash function is computed on selected message header data, which may include the computed MD5 value, a UTC time stamp, and/or other selected header data. Header data may comprise General Header data, Request Header data, Entity Header data, etc. as defined by a HTTP protocol standard. An example of General Header data is a cache-control directive. A Request Header may define operating parameters of an HTTP transaction, such as an Accept header field which defines the content types that are acceptable for a response (e.g., Accept: text/plain). Another example of a Request Header is a content length header which indicates the length of the request body in octets (e.g., Content-Length: 348). Entity-header fields may define length or other metadata about the entity-body or, if no body is present, about the resource identified by the request. The result is an HMAC value 70 which is transmitted along with the request message. The time stamp may be a proprietary header or use one of the header fields specified in a HTTP protocol standard. Use of a time stamp header may provide an indication whether the two communication pieces (sender and recipient) are synchronized in terms of time. For example, the recipient may be configured to verify that the time stamp is plus or minus a predetermined period of time (e.g., 2 seconds, 2 minutes, etc.) from actual time of day according to the recipient in order to consider the message valid.

In this exemplary embodiment, MD5 and SHA-1 algorithms are used. In alternative embodiments, these or other algorithms may be used at either or both stages 62 and 68, such as other one-way hash algorithms, SHA-0, RIPEMD, RIPEMD-128, RIPEMD-160, SHA-2, SHA-3, etc. In alternative embodiments, key-based or non-key based cryptographic hash functions, symmetric key encryptions, public key encryptions, or other encryption techniques may be used.

The MD5 digest algorithm may be used to verify the data integrity. The message sender may send the computed HMAC value within an Authorization header of the message for which the HMAC value has been computed. The Authorization header field may be one defined by Internet Engineering Task Force (IETF) Request for Comments 7235 or other RFCs, such as RFCs 7230, 7231, 7232, 7233, and 7234. Alternatively, the computed HMAC value may be inserted into a different header of the message, or a different portion of the message. Upon receipt of the message, the recipient computes an HMAC value for the same set of headers with the same pre-shared key that was used by the sender, in this case using the SHA-1 algorithm. If the received HMAC value and computed HMAC value are the same, the recipient accepts the message as coming from a known sender, otherwise the recipient discards the message.

In some embodiments, it is known by the recipient that no one has tampered with parts of the message (i.e. message body) that were used to compute the HMAC hash. In order to mitigate replay attacks, a UTC timestamp may be included in the message and the hash algorithm. The recipient may be configured to reject out-of-date messages or recently seen timestamp values.

Each client may have a pair of keys used to compute HMAC values. One key may be used for messages that a client sends to the server. The other key may be used for messages received from the server. The server may maintain a pair of keys for each configured client. One key may be used for messages that the server sends to the client. The other key may be used for messages received from the client. In one embodiment, the pre-shared keys may be provided to the clients and the server with an out-of-bands method during configuration, so that the keys are never sent directly between client and server. With the two keys mechanism, if either key is missing, the communications between the client and server will be broken.

Figure 5:
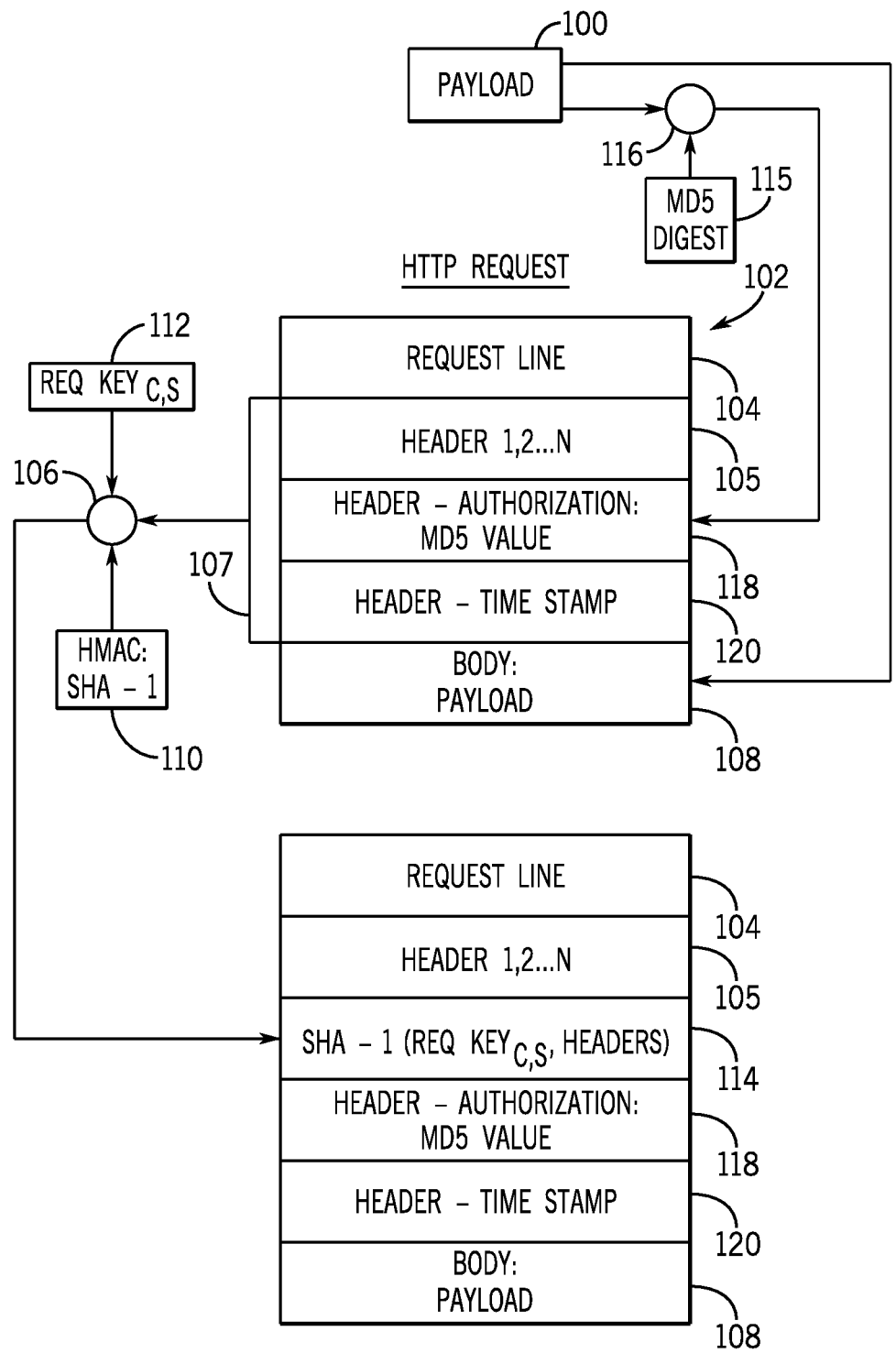
FIG. 5 is a data diagram illustrating the generation of a request message having certain fields, according to an illustrative embodiment.

Referring now to FIG. 5, a flow diagram of constructing or generating a request message will be described, according to an exemplary embodiment. The request message may be generated by a processing circuit of an infusion pump having improved network access security. At block 100, infusion pump data for transmission to a remote server computer may be generated. The infusion pump data may broadly include any data that is used by an infusion pump. In one example, the infusion pump data may comprise an indication of a mode the infusion pump is in. In other example, the infusion pump data may comprise a version of a data set that is programmed into the pump, a current time of day, a current infusion rate, an infusion event (such as the start of an infusion, the occurrence of a user exceeding a prestored soft limit of a particular programming parameter, a rate of an infusion, etc.). In some cases, the infusion pump data may comprise zeros or placeholder data used for the purpose of generating the request message. Infusion pump data may be an indication that no data is being transmitted as part of the payload. This "no data" indication may nevertheless be hashed. In still other embodiments, the infusion pump data may comprise pump history data, such as events, alerts, or other items of information indicating what took place on the infusion pump.

At block 102, the processing circuit is configured to generate a header portion of a request message having at least one field. A header portion may comprise any supplemental data placed at the beginning of a block of data being stored or transmitted. The header portion may be defined according to a predetermined format or specification, which may be a HTTP format, a proprietary format, etc. The header portion may comprise one field or a plurality of fields. In the case where the request message is to be an HTTP request, a request line 104 may be generated. A request line may comprise an identifier of the resource to be requested (e.g., a resource locator, such as a Universal Resource Locator), the protocol version in use, and/or other data.

A body portion 108 of the message may be generated. The body portion may comprise any payload data, such as infusion pump data.

At a block 106, the processing circuit may be configured to hash the header portion but not payload data or body portion using a cryptographic hash function 110 and a cryptographic key 112 to provide a hashed code 114. The hashed code may be inserted into the header portion of the request message. The infusion pump data may be inserted into the body portion of the request message, and the request message may be transmitted to the remote server computer over the communications network.

At a block 116, the processing circuit may further be configured to hash the payload (e.g., infusion pump data) using a second cryptographic function to provide a second hashed code 118. The second cryptographic function 115 may be the same function or a different function than the first cryptographic hash function 110. The second hashed code may be inserted into the header portion of the message, as shown at 118. The second hashed code may not only be hashed at block 106, but the second hashed code may also be transmitted in a header field (e.g., the Authorization header field of an HTTP message, or other field) in the final request message. In one example, the second hashed code 118 is hashed using the cryptographic hash function 110 and cryptographic key 112 to provide the hashed code.

In one example, the body or payload (e.g., comprising the infusion pump data) may be hashed without using a cryptographic key. This may significantly reduce processing resources, such as in the case of a large payload or a complicated encryption algorithm. In the specific example of FIG. 6, the MD5 is calculated only over the payload without using any keys, but before the payload becomes a payload portion of a message. This allows for modularity of the design. The MD5 value is stored into the Authorization header 118 and payload 100 is stored into request body 108.

As shown, the cryptographic function 110 may be a keyed-hash message authentication code SHA-1 algorithm. Cryptographic function 115 may be a keyless MD5 algorithm.

In some embodiments, the processing circuit may be configured to insert a time stamp 120 into the header portion of the request message. The time stamp may or may not be one of the selected headers which is hashed using the cryptographic hash function 110 and cryptographic key 112 to provide the hashed code 114. The time stamp may be a time of day, time/date indicator, UTC time stamp, and/or other time stamp.

In some embodiment, the request message may be transmitted using a protocol which is not a transport layer security (TLS) protocol or secure sockets layer (SSL) protocol. This may reduce the need for processing power, while still providing an acceptable level of security because of the hashing.

As shown, headers 105 may comprise additional headers, such as header 1, header 2 . . . header N. Bracket 107 indicates that selected headers may be used in the hash at block 106 in various different embodiments, such as only header 118, only header 120, both headers 118 and 120, all of headers 105, 118, 120, or other combinations. By selecting headers 118 and 120 for hashing at block 106, the message body is protected, even though the HMAC algorithm knows nothing about how it is protected.

A response message may be generated by a recipient, such as server computer 20, using one or more of the components described herein in FIGS. 2, 3, 4 and 5. For example, in a case where the request message asks for a new dataset for infusion pump 10, server computer 20 may be configured to retrieve from memory a stored infusion pump dataset for the infusion pump and generate a response message using one or more of the components described herein.

Figure 6:
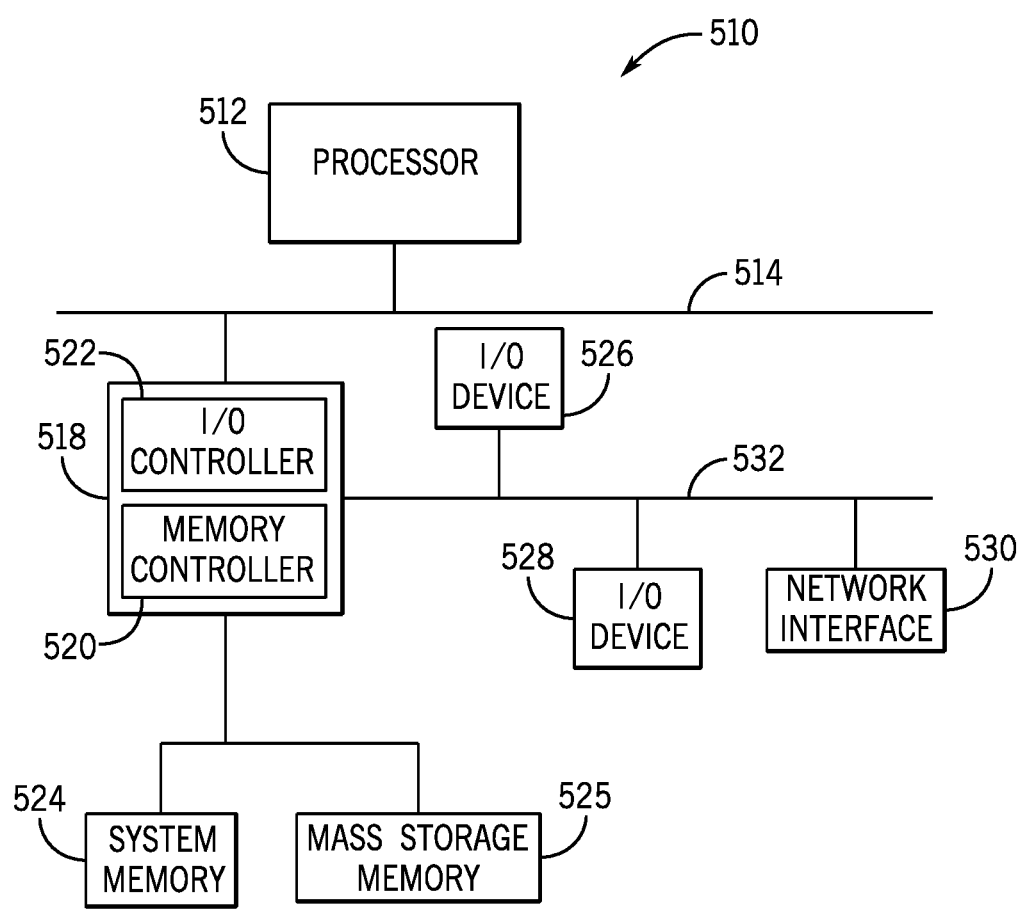
FIG. 6 is a block diagram of a computing device usable as client or server computer, according to an illustrative embodiment.

FIG. 6 is a block diagram of a server computer for processing infusion pump data for presentation on a display, according to an illustrative embodiment. In alternate embodiments, the systems and methods described herein may be implemented on a single server computer, a plurality of server computers, a server farm, a cloud server environment, or using other computer resources. Server 20 and infusion pump 10 may comprise analog and/or digital circuit components forming processing circuits configured to perform the steps described herein. The processing circuits may comprises discrete circuit elements and/or programmed integrated circuits, such as one or more microprocessors, microcontrollers, analog-to-digital converters, application-specific integrated circuits (ASICs), programmable logic, printed circuit boards, and/or other circuit components. Server 20 and infusion pump 10 each may comprise a network interface circuit configured to provide communications over one or more networks with each other and/or with other device. The network interface circuit may comprise digital and/or analog circuit components configured to perform network communications functions. The networks may comprise one or more of a wide variety of networks, such as wired or wireless networks, wide area-local-area or personal-area networks, proprietary or standards-based networks, etc. The networks may comprise networks such as an Ethernet network, networks operated according to Bluetooth protocols, IEEE 802.11x protocols, cellular (TDMA, CDMA, GSM) networks, or other network protocols. The network interface circuits may be configured for communication of one or more of these networks and may be implemented in one or more different sub-circuits, such as network communication cards, internal or external communication modules, etc.

According to one embodiment, storage of the infusion data records may be implemented on a database coupled to or part of server 20. The database may be a DBMS hosted on a server host platform, such as Microsoft Windows XP, Microsoft Windows Server 2008, etc.

Referring again to FIG. 6, a block diagram of an example processor system 510 is shown that can be used to implement systems, articles of manufacture, and methods described herein. As shown in FIG. 6, the processor system 510 includes a processor 512 that is coupled to an interconnection bus 514. The processor 512 can be any suitable processor, processing unit, or microprocessor, for example. Although not shown in FIG. 6, the system 510 can be a multi-processor system and, thus, can include one or more additional processors that are identical or similar to the processor 512 and that are communicatively coupled to the interconnection bus 514.

The processor 512 of FIG. 6 is coupled to a chipset 518, which includes a memory controller 520 and an input/output ("I/O") controller 522. A chipset may provide I/O and memory management functions as well as a plurality of general purpose and/or special purpose registers, timers, etc. that are accessible or used by one or more processors coupled to the chipset 518. The memory controller 520 performs functions that enable the processor circuit 512 (or processors if there are multiple processors) to access a system memory 524 and a mass storage memory 525.

The system memory 524 can include any desired type of volatile and/or non-volatile memory such as, for example, static random access memory (SRAM), dynamic random access memory (DRAM), flash memory, read-only memory (ROM), etc. The mass storage memory 525 can include any desired type of mass storage device including hard disk drives, optical drives, tape storage devices, etc.

The I/O controller 522 performs functions that enable the processor 512 to communicate with peripheral input/output ("I/O") devices 526 and 528 and a network interface 530 via an I/O bus 532. The I/O devices 526 and 528 can be any desired type of I/O device such as, for example, a keyboard, a video display or monitor, a mouse, etc. The network interface 530 can be, for example, an Ethernet device, an asynchronous transfer mode device, an 802.11 device, a DSL modem, a cable modem, a cellular modem, etc. that enables the processor system 510 to communicate with another processor system.

While the memory controller 520 and the I/O controller 522 are depicted in FIG. 6 as separate blocks within the chipset 518, the functions performed by these blocks can be integrated within a single semiconductor circuit or can be implemented using two or more separate integrated circuits.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a tangible machine accessible or readable medium and executable by, for example, a processor system (e.g., the example processor system 510 of FIG. 6). Tangible computer readable media include a memory, DVD, CD, etc. storing the software and/or firmware, but do not include a propagating signal.

As used herein, the term tangible computer readable medium includes any type of computer readable storage and excludes propagating signals. Additionally or alternatively, the example processes described herein may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information).

Certain embodiments described herein can omit one or more of the method steps and/or perform the steps in a different order than the order listed. For example, some steps cannot be performed in certain embodiments. As a further example, certain steps can be performed in a different temporal order, including simultaneously, than listed above.

While the exemplary embodiments have been described with reference to an infusion pump, the teachings herein may be applied to other medical devices, such as apheresis devices (e.g., plasmapheresis, blood therapy, etc.) or other devices that are invasive or noninvasive, that interface with a human patient via a needle in the patient's skin, insulin pumps (e.g., internal or external to the body cavity), medical imaging devices (e.g., CT scanners, x-ray imagers, magnetic resonance imaging). The teachings may also be applied outside the medical field to any computing devices requiring an improved security solution, such as mobile phones, tablet computers or other computers configured to be operated while held in a human hand, laptops, personal computers, and other networked computers.

While the embodiments have been described with reference to certain details, it will be understood by those skilled in the art that various changes can be made and equivalents can be substituted without departing from the scope described herein. In addition, many modifications can be made to adapt a particular situation or material to the teachings without departing from its scope. Therefore, it is intended that the teachings herein not be limited to the particular embodiments disclosed, but rather include additional embodiments falling within the scope of the appended claims.

The invention claimed is:

1. An infusion pump having improved network access security, comprising:
    a network interface circuit configured to provide communications over a network; and
    a processing circuit configured to:
        generate infusion pump data for transmission to a remote server computer;
        generate a header portion of a request message having at least one field;
        hash the infusion pump data using a first cryptographic function to provide a first hashed code;
        insert the first hashed code into the header portion of the request message;
        hash the header portion but not payload data using a second cryptographic hash function and a cryptographic key to provide a second hashed code, wherein the second cryptographic function may be the same function or a different function than the first cryptographic hash function;
        insert the second hashed code into the header portion of the request message;
        insert the infusion pump data into a body portion of the request message; and
        transmit the request message to the remote server computer over the communications network.

2. The infusion pump of claim 1 wherein the second cryptographic function is the same function as the first cryptographic hash function.

3. The infusion pump of claim 1, wherein the second hashed code is inserted into an Authorization header field defined by Internet Engineering Task Force (IETF) Request for Comments 7235.

4. The infusion pump of claim 1, wherein the infusion pump data is hashed without using any cryptographic key.

5. The infusion pump of claim 4, wherein the second cryptographic hash function is a keyed-hash message authentication code SHA-1 algorithm, wherein the first cryptographic function is an MD5 algorithm.

6. The infusion pump of claim 1, wherein the processing circuit is configured to:
    insert a time stamp into the header portion of the request message.

7. The infusion pump of claim 6, wherein the time stamp is hashed using the second cryptographic hash function and the cryptographic key to provide the first hashed code.

8. The infusion pump of claim 1, wherein the cryptographic key is a shared cryptographic key which is shared between the infusion pump and the remote server computer out of band.

9. The infusion pump of claim 1, wherein the request message is a hypertext transfer protocol request message comprising a request line, the header portion and a body comprising the infusion pump data.

10. The infusion pump of claim 9, wherein the infusion pump data comprises an indication that an infusion has been started and a flow rate of the infusion.

11. The infusion pump of claim 1, wherein the request message is transmitted using a protocol which is not a transport layer security protocol or secure sockets layer protocol.

12. A server computer for responding to a request message from an infusion pump, comprising:
 a network interface circuit configured to provide communications over a network; and
 a processing circuit configured to:
  store an infusion pump dataset for transmission to the infusion pump;
  receive a request message from the infusion pump;
  generate a header portion of a response message having at least one field;
  hash the infusion pump dataset using a first cryptographic hash function to provide a first hashed code;
  insert the first hashed code into the header portion of the message;
  hash the header portion but not payload data using a second cryptographic hash function and a cryptographic key to provide a second hashed code, wherein the second cryptographic hash function may be the same function or a different function than the first cryptographic hash function;
  insert the second hashed code into the header portion of the response message;
  insert the infusion pump dataset into a body portion of the response message; and
  transmit the response message to the infusion pump over the network.

13. The server computer of claim 12, wherein the first hashed code is hashed using the second cryptographic hash function to provide the hashed code.

14. The server computer of claim 12, wherein the second hashed code is inserted into an Authorization header field defined by Internet Engineering Task Force (IETF) Request for Comments 7235.

15. The server computer of claim 13, wherein the second cryptographic hash function is a keyed-hash message authentication code SHA-1 algorithm, wherein the first cryptographic function is an MD5 algorithm.

16. The server computer of claim 12, wherein the processing circuit is configured to:
 insert a time stamp into the header portion of the request message, wherein the time stamp is hashed using the cryptographic hash function and cryptographic key to provide the hashed code.

17. The server computer of claim 12, wherein the response message is transmitted using a protocol which is not a transport layer security protocol or secure sockets layer protocol.

18. An infusion pump having improved network access security, comprising:
 a memory configured to store infusion pump data;
 a pump configured to pump a medicament to a human patient;
 a network interface circuit configured to provide communications over a network; and
 a processing circuit configured to control the pump and to:
  retrieve infusion pump data from the infusion pump memory for transmission to a remote server computer;
  hash the infusion pump data using a first cryptographic function to provide a first hashed code,
  generate header data for a header portion of a Hypertext Transfer Protocol request message,
  generate a time stamp;
  hash the header data, the time stamp and the first hashed code using a second cryptographic hash function and a cryptographic key to provide a second hashed code for the header portion, wherein the first cryptographic function is the same as or different than the second cryptographic hash function, wherein the cryptographic key is a shared cryptographic key which is shared between the infusion pump and the remote server computer out of band;
  insert the second hashed code into the header portion of the Hypertext Transfer Protocol request message;
  insert the infusion pump data into a body portion of the Hypertext Transfer Protocol request message;
  generate a request line for the Hypertext Transfer Protocol request message; and
  transmit the Hypertext Transfer Protocol request message to the remote server computer over the communications network.

* * * * *